United States Patent [19]

Joyce et al.

[11] Patent Number: 5,076,284

[45] Date of Patent: Dec. 31, 1991

[54] FLUIDIC HEART-SOUND MONITOR AND ESOPHAGEAL STETHOSCOPE

[75] Inventors: James W. Joyce, Rockville; Nassy Srour, Silver Spring, both of Md.; Michael V. Scanlon, Springfield, Va.; Stephen M. Tenney, Rockville; George Mon, Potomac, both of Md.; John P. Gills, Washington, D.C.

[73] Assignee: The United States of America as represented by the Secretary of the Army, Washington, D.C.

[21] Appl. No.: 607,432

[22] Filed: Oct. 23, 1990

[51] Int. Cl.$^5$ .................................................. A61B 7/02
[52] U.S. Cl. ...................................... 128/773; 128/715
[58] Field of Search ................ 128/715, 773; 381/156, 381/161, 165, 166; 434/266

[56] References Cited

U.S. PATENT DOCUMENTS

| | | | |
|---|---|---|---|
| 2,699,465 | 1/1955 | Hamilton | 128/715 |
| 3,185,778 | 5/1965 | Giannini et al. | 381/156 |
| 3,732,631 | 5/1973 | Petrovick | 434/366 |
| 4,248,241 | 2/1981 | Taechi | 128/715 |

Primary Examiner—William E. Kamm
Attorney, Agent, or Firm—Saul Elbaum; Freda L. Krosnick

[57] ABSTRACT

A heart-sound monitor and esophageal stethoscope which makes use of fluidic laminar proportional amplifiers (LPAs). These LPA's are used to sense and amplify incoming acoustic pressure signals, such as heart signals. Moreover, the fluidic monitor is able to monitor a fetus heartbeat while eliminating the acoustic interference present from the mother's heartbeat. In this case, the LPA acts not only as an amplifier, but as an acoustic filter as well.

6 Claims, 4 Drawing Sheets

FLUIDIC HEART-SOUND MONITOR AND ESOPHAGEAL STETHOSCOPE

RIGHTS OF THE GOVERNMENT

The invention described herein may be manufactured, used and licensed by or for the U.S. Government without payment to us of any royalty thereon.

BACKGROUND OF THE INVENTION

Heart-sound monitors and esophageal stethoscopes are used to monitor heart sounds and other body functioning sounds. Many of these devices currently available are expensive, fragile, and inefficient to clearly convey the sounds of the body one wishes to accurately monitor.

Moreover, some prior art heart-sound monitors use ultrasound, and therefore the patient is subjected to extended ultrasonic signals. Although to date the use of ultrasound appears to have no adverse effects on the patient, controversy in this area does exist. It would, therefore, appear to be desirable to develop a device to replace the ultrasound apparatus wherein any possible safety issues associated with ultrasonic amplitude and duration can be eliminated.

The present invention has been developed to create a heart-sound monitor and esophageal stethoscope which uses a non-electronic microphone whose sensitivity is greater than that currently available from the present day microphones used in the monitoring art. The invention herein provides for a low cost, rugged and efficient heart monitoring apparatus.

BRIEF SUMMARY OF THE INVENTION

This invention deals with a heart-sound monitor and esophageal stethoscope which makes use of fluidic laminar proportional amplifiers (LPA's). The fluidic LPAs serve the function of a microphone for use in medical apparatus of the present invention. These LPA's are used to sense and amplify incoming acoustic pressure signals, such as heart signals. These amplifiers use the interaction of air jets to amplify the sound they receive from the incoming acoustic pressure signals. The LPA is a non-electronic "microphone" whose sensitivity is greater than the sensitivity of most instrumentation grade electronic microphones already available. Moreover, fluidic sensors are much less expensive than highly-sensitive, electronic microphones; and they are virtually indestructible since they are made of essentially a monolithic block of material containing no moving parts.

Use of the present invention allows one to sense and amplify heart sounds, breathing sounds, and other bodily sounds that have not previously been detectable. All sounds amplified by an LPA "microphone" are very clear and sharp sounding. This is due to the fact that an LPA, because it is fluidic and non-electronic, does not produce any noise interference. Noise interference is present and inherent to electronic microphones. Therefore, the use of an LPA is more efficient because it is able to pick up on certain acoustic levels which would be drowned out by noise or too slight to overcome the noise interference present in an electronic microphone. Generally speaking, these fluidic "microphones" have higher dynamic range than the conventional electronic microphones.

Being able to detect and amplify the heart and body function sounds will aid a medical practitioner in his/her everyday practice of medicine. It will aid to significantly improve the accuracy of data obtained during examinations of patients, during surgery, child delivery, prenatal care, etc. Moreover, the present invention may be used to provide assistance in the instructional and educational/consultational environments.

An LPA, contrary to an ultrasound apparatus, is passive in that it does not emit energy or ultrasonic waves to the patient. The LPA's low cost, ruggedness, and passivity makes for an attractive component to use in situations where equipment is likely to get damaged or mistreated (i.e. emergency vehicles).

By using the present invention, the heart sounds and other bodily sounds can be broadcasted through an acoustical system or through a loudspeaker horn. This would be advantageous under numerous circumstances. For example, it would enable an entire surgical team to listen to and monitor the heart beat and breathing pattern of a patient during a surgical procedure. Use of the invention would enable an entire family to hear the heart beat of a fetus in womb. Such a device could be used as an instructional aid during medical examinations and health discussions with patients, allowing both the patient and the health professional to listen and discuss certain heart and breathing patterns of the patient. Moreover, in an emergency situation, time is a critical factor; the time involved in allowing all important medical personnel to listen through a single stethoscope could possibly be fatal to the patient.

It is an object of the present invention to provide a fluidic esophageal stethoscope and a fluidic heart-sound monitor.

It is a further object of the invention to provide a more sensitive heart and breathing monitor device.

It is a further object of the invention to provide an apparatus for sensing and amplifying heart and breathing sounds that were not detectable by prior art means.

Still a further object of the invention is to provide a non-electronic device which can allow more than one person to hear and monitor various bodily sounds.

Other objectives and features of the present invention will be apparent from the following detailed description of the invention.

DETAILED DESCRIPTION OF THE INVENTION

The invention herein deals with a fluidic heart-sound monitor and esophageal stethoscope. The above-mentioned objectives are met by use of the present invention.

The present invention utilizes the well-known fluidics technology in the medical device field. The application of fluidics in the medical industry has tremendous potential. Fluidic devices, such as Laminar Proportional Amplifiers (LPAs), are made essentially of a monolithic block of metal, polymeric or rubber materials, such as stainless steel, polycarbonate, or materials having like properties. Because fluidic devices contain no moving parts, they are, for all practical purposes, virtually indestructible. This particular property increases the life and efficiency of any medical device incorporating a fluidic component. An additional attribute of fluidic devices is that they are relatively inexpensive as compared to their electronic counterparts. Moreover, because there are no moving parts therein and because the flow through said LPAs is laminar, the fluidic device itself does not contribute any noise interference; therefore, the device is able to easily and readily detect and amplify all bodily sounds.

One embodiment of the present invention entails the incorporation of a fluidic LPA into conventional heart-sound monitors and esophageal stethoscopes. A fluidic LPA can be inserted into, for example, a conventional stethoscope, between a conventional chestpiece and a conventional pneumatic headset. Acoustic pressure signals, i.e. heart sounds, felt by a conventional stethoscope chestpiece are transmitted through a plastic, flexible tubing to an input port of a fluidic gain block (herein referred to as "LPA"). The acoustic pressure signals then pass through the LPA and exit at the output ports of the same and are fed into a pneumatic headset (i.e., stethoscope earpieces). See, for example, FIG. 2.

Use of the LPA in the stethoscope described above increases the amplitude of the acoustical sound as well as increasing the sound quality of the signals. The fluidic device incorporated into the heart-sound monitor and the esophageal stethoscope of the present invention improves the effectiveness of said apparatus. A fluidic LPA can be incorporated into a conventional, acoustical monitoring apparatus and have the same enhancing effect.

The above embodiment of the present invention can be extended by using a plurality or series of connected fluidic LPAs to further enhance the clarity and efficiency of sound retrieval. Moreover, an additional modification to the above embodiment may comprise the addition of a conventional loudspeaker, electronic microphone and/or tape recorder to the monitoring system. See, for example, FIG. 4. These various embodiments of the present invention will be more clearly set forth and described in the drawings herein and the descriptions thereof.

The flexible, tubing material used to connect the individual components of the present invention (i.e. chestpiece, fluidic LPA, earpieces, etc.) may be composed of PVC (polyvinyl chloride), vinyl, silicon, rubber, and materials having like properties. These tubings may have an inside diameter ranging from about 0.5 mm to about 10 mm. Any conventional stethoscope-type, flexible tubings may be used within the purview of the invention herein. Moreover, the chestpieces and earpieces incorporated as part of the apparatus are state of the art component parts. The novelty in the embodiments described above resides in the incorporation of a fluidic LPA into a heart-sound monitoring device. The other components of the monitoring apparatus are conventional and within the skill of the artisan.

An additional variation to the same theme, within the scope of the present invention, involves employing a fluidic LPA to amplify a fetal heartbeat while eliminating any noise created by the mother's heartbeat. In this embodiment, the fluidic LPA not only serves as a "microphone," but also serves as an acoustic filter means. FIG. 5, herein, illustrates this variation. For instance, a heart-sound monitor may comprise two chestpieces. The first chestpiece is placed on the mother's chest and said chestpiece is connected through rubber tubing to input port A of the fluidic LPA; the second is placed on the mother's abdomen to pick up the baby's heartbeat. The second chestpiece will also register, in addition to the fetal heartbeat, a faint heartbeat from the mother. Said second chestpiece is connected through a second, flexible rubber tubing to input port B of the LPA. In the first chestpiece, the mother's heartbeat is sensed; the second chestpiece, as previously stated, registers both the mother's and the baby's heartbeat. The amplitude of the mother's heartbeat from the first chestpiece can be adjusted using a conventional acoustic resistor to balance the amplitude of the mother's heartbeat at both input ports A and B of the fluidic LPA. The fluidic LPA would then operate to cancel out the mother's heartbeat sensed at each of the individual input ports. This results in the baby's heartbeat being the sole output of the fluidic heart-sound monitor. This fetal monitor enables doctors, as well as, parents and siblings to hear only the fetal heartbeat without any interference from the mother's heartbeat. To this fetal monitor, variations may be made, such as the incorporation of a conventional loudspeaker, a conventional tape recorder, etc.

The fetal heart-sound monitor herein can also monitor other bodily sounds other than heartbeats. It is able to monitor fetal movement. An LPA is extremely sensitive in detecting very low frequency sounds. Since the response of an LPA is capable of sensing frequencies to approximately zero Hertz, very low-frequency sounds associated with slow movements can be detected, heard and amplified by the apparatus of the present invention. In the medical profession, movement of a fetus is considered to be an indication of health; therefore, the ability to monitor fetal movement is valuable.

The tubes, chestpieces and earpieces employed in the fetal monitor are conventional to the stethoscope art.

The fluidic LPA which may be incorporated into the invention has the conventional configuration of an LPA—see FIG. 1. The fluidic LPA may be composed of a variety of compatible materials, such as metals, plastics, ceramics, and materials having like properties. Although fluidic LPAs can be configured to have any size or geometry, they are built to accommodate the specific amplifying needs of the user. Currently, conventional LPAs have dimensions along the lines of approximately 23 mm in length, 0.25 mm in height and 23 mm in width.

The specific features of the present invention will be further described and explained in reference to the accompanying drawings and specific embodiments.

DETAILED DESCRIPTION OF THE DRAWINGS

The invention may be better understood and described by making reference to FIGS. 1-5. FIGS. 1-5 merely teach a few embodiments of the present invention. The invention herein is not limited to these variations of the heart-sound monitor and esophageal stethoscope.

Figure 1:
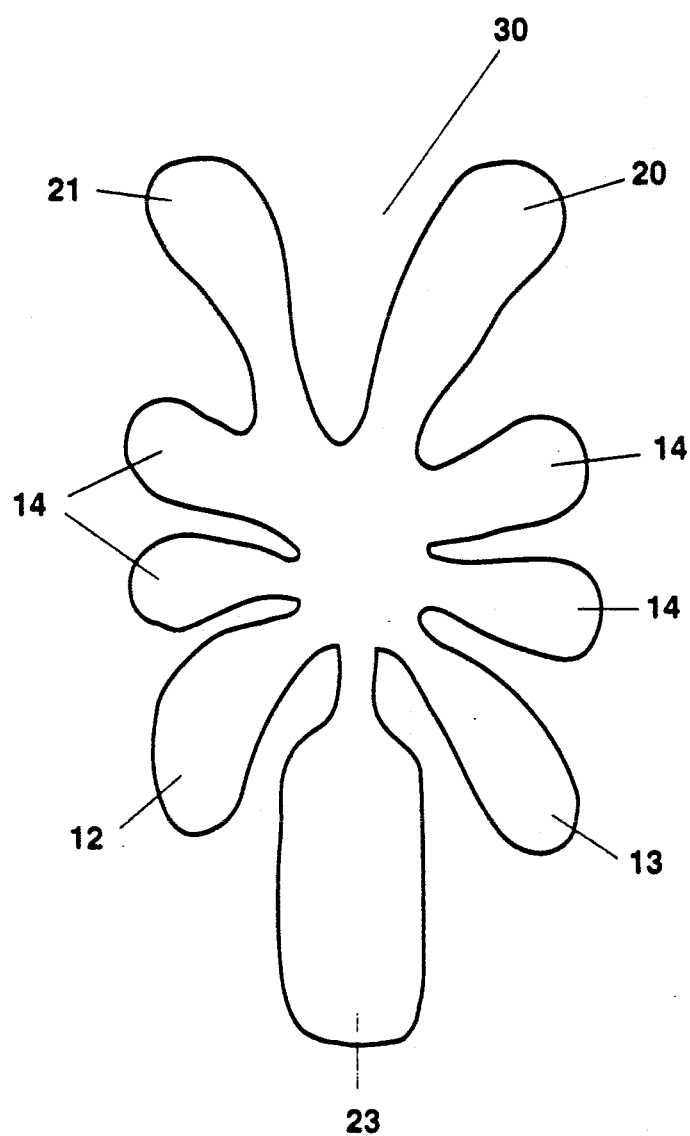
FIG. 1 is a representation of a conventional fluidic laminar proportional amplifier (LPA).

FIG. 1 illustrates a conventional fluidic laminar proportional amplifier (LPA) 30 which may be used as the amplifier in the present invention. The fluidic LPA 30 has conventional pressure supply port 23, input ports 12 and 13, vent ports 14 and outpot ports 20 and 21. A variation to this conventional LPA 30 may be made wherein only one input port is present. In the present invention, acoustic input from a stethoscope chestpiece (not shown) is transmitted to input ports 12 and 13. Said acoustic input is driven by a pressure supply supplied at pressure supply port 23. The acoustic input is driven through output ports 20 and 21, which may be connected to a conventional stethoscope headset, a conventional loudspeaker, a conventional tape recorder, a conventional electronic microphone, or another fluidic LPA. FIGS. 2-5 illustrate the incorporation of said LPAs into acoustic monitoring devices.

Figure 2:
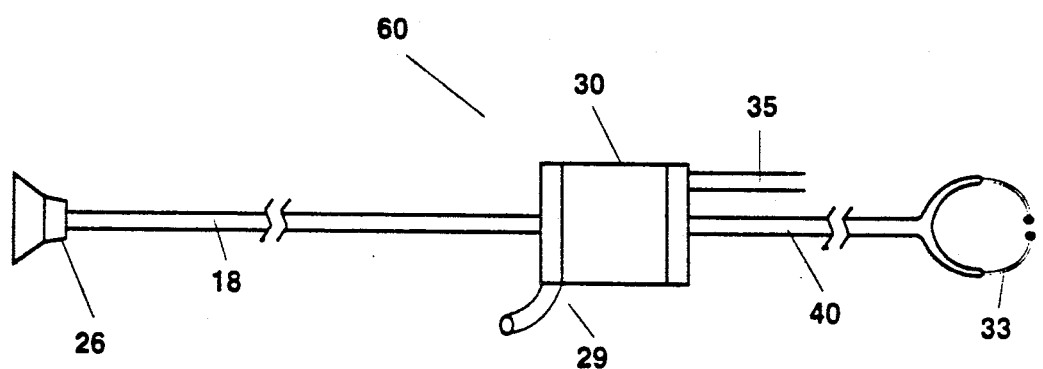
FIG. 2 illustrates one of the heart-sound monitoring devices within the scope of the present invention.

FIG. 2 illustrates one embodiment within the scope of the present invention. The stethoscope 60 is the most elementary application of the present invention. Stethoscope 60 comprises a chestpiece 26 which is connected through flexible, rubber tubing 18 to the input ports of gain block 30 (which is a fluidic LPA). The acoustic sounds sensed by chestpiece 26 are transferred through gain block 30 and exit through the output ports of said gain block 30. The output ports allow the amplified acoustic input to travel through tubes 35 and 40. Either output tube (35 or 40) may be connected to a stethoscope headset, a loudspeaker, or a tape recorder, or any combination of these. In the simplest case, one tube (e.g. tube 40) would be connected to a stethoscope headset (as shown in FIG. 2), and the other output tube (tube 35) would not be used. Through headset 33 one can hear an amplification of the acoustic sound sensed at chestpiece 26. Pressure supply to drive the fluidic LPA 30 is provided by a regulated compressed air source, such as an electric pump, through pressure supply tube 29. (Note that FIG. 1 illustrates a more detailed fluidic LPA. The pressure supply port, input ports, output ports, etc. illustrated in FIG. 1 are present within fluidic LPA 30 in all of the figures.)

Figure 3:
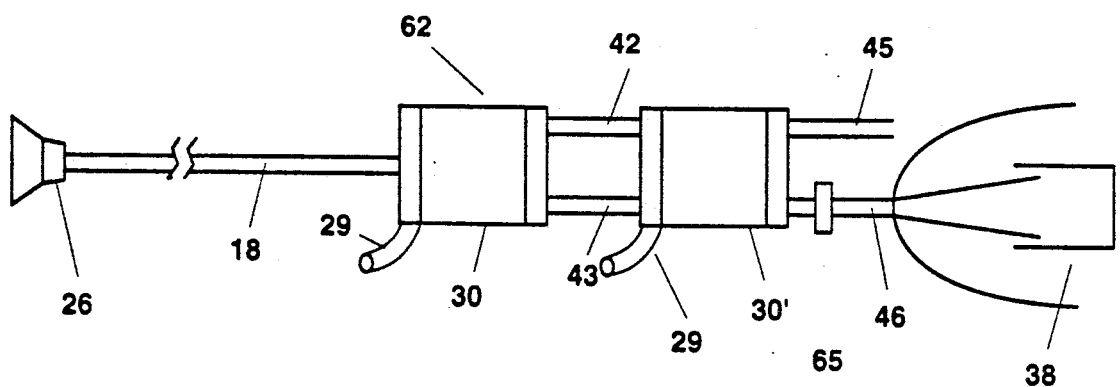
FIG. 3 illustrates a second embodiment of a heart-sound monitoring device within the present invention.

FIG. 3 illustrates a second embodiment of a heart-sound monitor within the scope of the present invention. FIG. 3 is a variation to the stethoscope depicted in FIG. 2. The heart-sound monitor 62 herein, as does the stethoscope 60 in FIG. 2, comprises a chestpiece 26, flexible tubing 18 connecting the chestpiece 26 to gain block 30. In the heart-sound monitor 62 depicted in FIG. 3, however, the output of gain block 30, which travel through tubes 42 and 43, runs into the input ports of a second fluidic LPA 30' which acts to further amplify the signals obtained by the chestpiece 26. The amplified acoustic signals travel through fluidic LPA 30', through a pressure-to-electrical transducer 65 and through tubes 45 and 46, which can be used just as described in the embodiment shown in FIG. 2 for tubes 35 and 40 therein. Here tube 46 is shown connected to a loudspeaker 38. Pressure supply to drive the fluidic LPAs 30 and 30' is provided to pressure supply tube 29 by a regulated compressed air source, as previously set forth. (Again, FIG. 1 illustrates a more detailed fluidic LPA. The pressure supply port, input ports, output ports, control ports, etc. illustrated in FIG. 1 are present within the fluidic LPAs 30 and 30' herein.)

Figure 4:
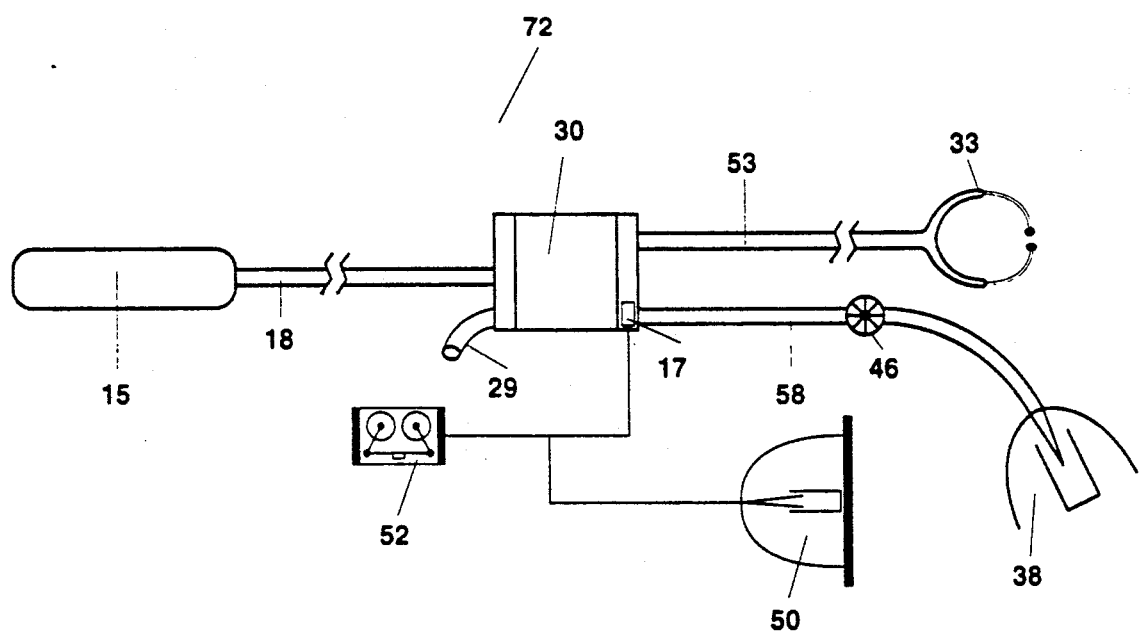
FIG. 4 illustrates an embodiment of an esophageal stethoscope within the scope of the invention.

A more elaborate embodiment of the present invention is set forth in FIG. 4. FIG. 4 illustrates an esophageal stethoscope 72 within the scope of the present invention. The esophageal stethoscope 72 makes use of a conventional esophageal tube 15 which is connected to a fluidic gain block 30 through flexible-tubing 18. Flexible tubing 18 transmits the acoustic signal picked up by the esophageal tube 15 to gain block 30, which in turn provides an output acoustic signal through various conventional apparatus—i.e. a stethoscope headset 33, a loudspeaker 38, an electronic microphone 17, a remote speaker 50 and/or a tape recorder 52. The acoustic output is transmitted to the various conventional apparatus by flexible tubings 53 and 58 which are connected to the output ports of the fluidic gain block 30 (FIG. 1 illustrates the gain block in more detail).

As part of the embodiment depicted in FIG. 4, one can record the acoustic signals picked up by the esophageal tube 15 by the use of a conventional tape recording device 52. Moreover, the conventional apparatus need not be operated simultaneously. For instance, an on/off switch, such as the one set forth as 46, may be placed on any and all of the output transmitting tubes 53 and 58. Moreover, any of these conventional apparatus may be removed from the esophageal stethoscope 72. An esophageal stethoscope 72 within the scope of the present invention may make use of a conventional stethoscope headset 33 and/or a conventional loudspeaker 38 and/or a conventional remote speaker 50 and or a conventional tape recorder 52. One or more acoustic relaying sources may be used. In addition, any conventional electronic microphone 17 may be incorporated into said apparatus.

Figure 5:
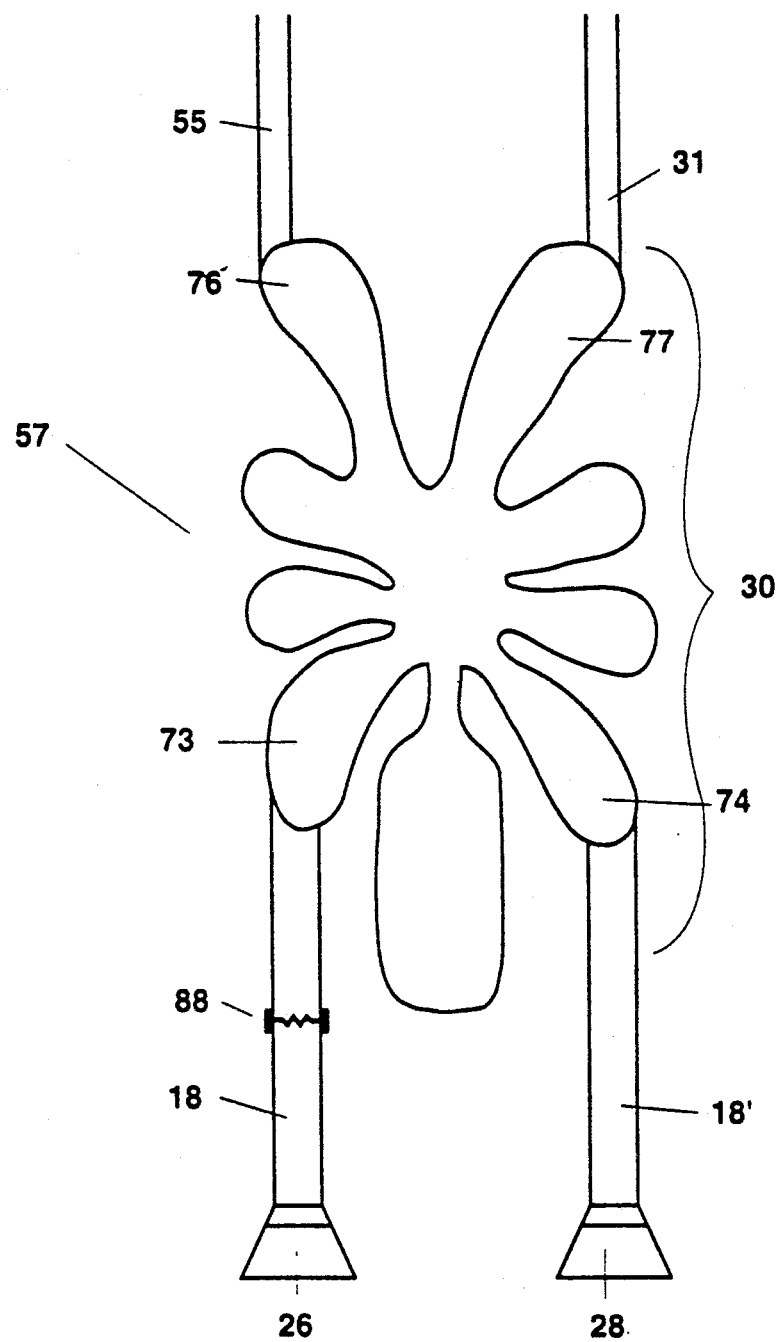
FIG. 5 is a representation of a fetal monitor of the invention.

FIG. 5 illustrates a fetal heart-sound monitor 57 within the scope of the present invention. The fetal heart-sound monitor 57 comprises two chestpieces 26 and 28 which are individually attached through two flexible tubings 18 and 18'. Note that flexible tube 18 is equipped with a conventional acoustic resistor 88 to balance the acoustic amplitudes of the mother's heartbeat which may be sensed at both of the chestpieces 26 and 28. Each of the separate flexible tubings 18 and 18' are connected to fluidic LPA (gain block) 30 through input ports 73 and 74. Output ports 76 and 77 are connected to flexible tubings 55 and 31, respectively. These flexible tubings 55 and 31 may then be hooked up to conventional acoustic relaying sources, such as those set forth in FIGS. 2-4 (i.e., a stethoscope headset, a loudspeaker, a microphone, etc.).

The fetal heart-sound monitor 57 operates in the following fashion: Chestpiece 26 is held against the mother's chest; chestpiece 28 is held against the mother's abdomen in order to detect the fetus' heartbeat. The acoustic signal from each of the chestpieces 26 and 28 is transmitted through flexible tubings 18 and 18' to the fluidic LPA 30. The fluidic LPA 30, here, acts as an amplifier and as an acoustic filter. How it acts as a fluidic amplifier is well known to one skilled in the art of fluidics. It acts as an acoustic filter in that the *only* acoustic output which can be sensed and detected using this apparatus will be the heartbeat of the fetus. The mother's heartbeat will be sensed by each of the chestpieces 26 and 28. Chestpiece 26 senses the mother's heartbeat directly because it is placed on the mother's chest; chestpiece 28 senses the mother's heartbeat indirectly through the bodily sounds picked up by chestpiece 28 which is placed on the mother's abdomen. Any duplicated sound entering each of the input ports 73 and 74, assuming equal amplitudes which can be adjusted using acoustic resistor 88, is cancelled by the fluidic LPA 30. This is a well known feature of LPAs. Therefore, the output signal of the fetal heart monitor within the scope of the present invention is the heartbeat of the baby in utero.

Note that FIG. 5 incorporates an acoustic resistor 88 to assure that the amplitude of the sensed mother's heartbeat from chestpiece 26 is equivalent to the amplitude of the sensed mother's heartbeat from chestpiece 28. Any conventional acoustic resistor may be incorporated herein. An acoustic resistor functions to adjust the amplitude of the incoming sound signal. One having skill in the art would be able to properly operate said acoustic resistor. The novelty of the present invention does not reside in the use of a conventional stethoscope headset, or in the incorporation of a conventional loudspeaker or remote speaker, etc. A novelty of the invention rests with the incorporation of fluidic LPAs into a heart and body function acoustical monitoring devices. In addition, through the incorporation of a fluidic LPA into a fetal heart-sound monitor of the type described herein, one is able to more accurately monitor the heartbeat of a fetus in womb without any interference from the mother's heartbeat.

The embodiments set forth in the figures are merely illustrative of the monitoring devices within the scope of the present invention. It will be obvious to those skilled in the art that changes and modifications may be made to the monitoring apparatus without departing from the spirit of this invention.

EXAMPLE

A heart monitoring device was built using a stethoscope chestpiece manufactured by Medical Products Division of 3M under the name of Anesthescope ®. The chestpiece was connected to a flexible rubber tubing having an internal diameter of approximately 3 mm, a thickness of about 2 mm, and a length of about 45 cm. The flexible tubing is connected to a fluidic LPA manufactured by The U.S. Department of the Army at Harry Diamond Laboratory. Said LPA has the following dimensions: 23 mm in length; 23 mm in width and 0.25 mm in thickness. The input and output ports are of such a size as to accommodate the needs required by the apparatus. The output ports of the LPA used are connected to additional rubber tubing which is then connected to a conventional stethoscope headset, such as the one manufactured by AVID Corporation (typical airline headset).

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

We claim:

1. A medical acoustic monitoring device comprising means for sensing the acoustic signal from a patient; a fluidic laminar proportional amplifier;
flexible tubing means connecting said sensing means to said fluidic laminar proportional amplifier, said tubing means for transmitting said acoustic signal to said fluidic laminar proportional amplifier;
an acoustic relaying device; and
additional tubing means connecting said amplifier to said acoustic relaying device for transmitting an amplified acoustic signal from said fluidic laminar proportional amplifier to said acoustic relaying device.

2. The medical acoustic monitoring device in accordance with claim 1, wherein said means for sensing the acoustic signal from a patient is a stethoscope chestpiece.

3. The medical acoustic monitoring device in accordance with claim 1, wherein said acoustic relaying device may be a stethoscope headset.

4. The medical acoustic monitoring device in accordance with claim 1, wherein said means for sensing the acoustic signal from a patient is an esophageal tube.

5. The medical acoustic monitoring device in accordance with claim 1, wherein said acoustic relaying device may be a loudspeaker.

6. The medical acoustic monitoring device in accordance with claim 1, wherein said acoustic relaying device may be a tape recorder.

* * * * *